US007951969B2

(12) United States Patent
Karch et al.

(10) Patent No.: US 7,951,969 B2
(45) Date of Patent: May 31, 2011

(54) PROCESS FOR THE PREPARATION OF IRIDIUM ACETATE

(75) Inventors: Ralf Karch, Kleinostheim (DE); Bernd Kayser, München (DE); Andreas Rivas-Nass, Budenheim (DE); Jürgen Bodo Widmer, Darmstadt (DE); Roland Winde, Frankfurt (DE); Eileen Wörner, Maintal (DE)

(73) Assignee: Umicore AG & Co. KG, Hanau (DE)

( * ) Notice: Subject to any disclaimer, the term of this patent is extended or adjusted under 35 U.S.C. 154(b) by 491 days.

(21) Appl. No.: 11/915,084

(22) PCT Filed: May 24, 2006

(86) PCT No.: PCT/EP2006/004964
§ 371 (c)(1),
(2), (4) Date: May 12, 2008

(87) PCT Pub. No.: WO2006/125628
PCT Pub. Date: Nov. 30, 2006

(65) Prior Publication Data
US 2010/0234628 A1    Sep. 16, 2010

(30) Foreign Application Priority Data

May 25, 2005 (DE) .......................... 10 2005 024 116
Jun. 16, 2005 (DE) .......................... 10 2005 027 954

(51) Int. Cl.
*C07F 15/00* (2006.01)
*B01J 31/00* (2006.01)

(52) U.S. Cl. ........................................................ 556/136
(58) Field of Classification Search ................... 556/136
See application file for complete search history.

(56) References Cited

FOREIGN PATENT DOCUMENTS

| EP | 1 046 629 | 10/2000 |
| GB | 2 413 323 A * | 10/2005 |
| WO | WO 96/23757 | 8/1996 |

OTHER PUBLICATIONS

EPO Machine language English translation of EP 1 046 629 A1 (Jul. 2010).*

* cited by examiner

*Primary Examiner* — Porfirio Nazario Gonzalez
(74) *Attorney, Agent, or Firm* — Smith, Gambrell & Russell, LLP

(57) ABSTRACT

The present invention relates to a process for the preparation of indium acetate comprising the steps: (a) reacting an indium compound with an alkaline compound in a protic solvent to obtain an iridium containing precipitate, where the reaction is conducted in the presence of at least one component (i) selected from oxalic acid, a salt of oxalic acid, formic acid and a salt of formic acid, (b) reacting the precipitate in the presence of at least (i) one compound selected from oxalic acid, a salt of oxalic acid, formic acid and a salt of formic acid, and (ii) $CH_3CO_2H$ and/or $CH_3(CO)O(CO)CH_3$ to give an iridium acetate containing solution. The invention also relates to indium acetate having a low halide content, to an indium containing precipitate and to uses of the iridium containing precipitate of the present invention and the iridium acetate of the present invention.

30 Claims, 2 Drawing Sheets

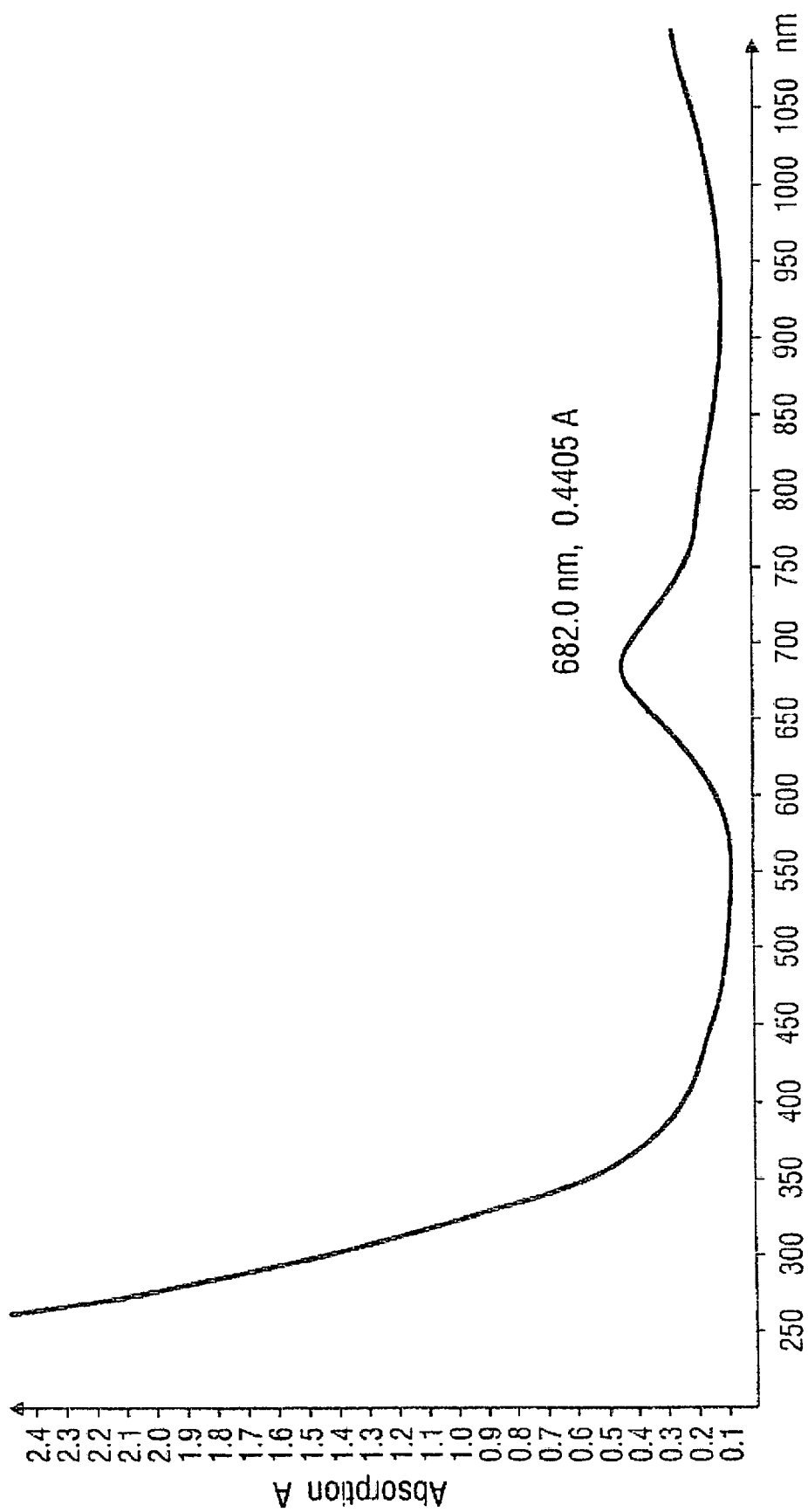
Fig. 1: Ultraviolet/visible spectrum of the compound obtained in the comparative example (0.61 mg/ml in DI water)

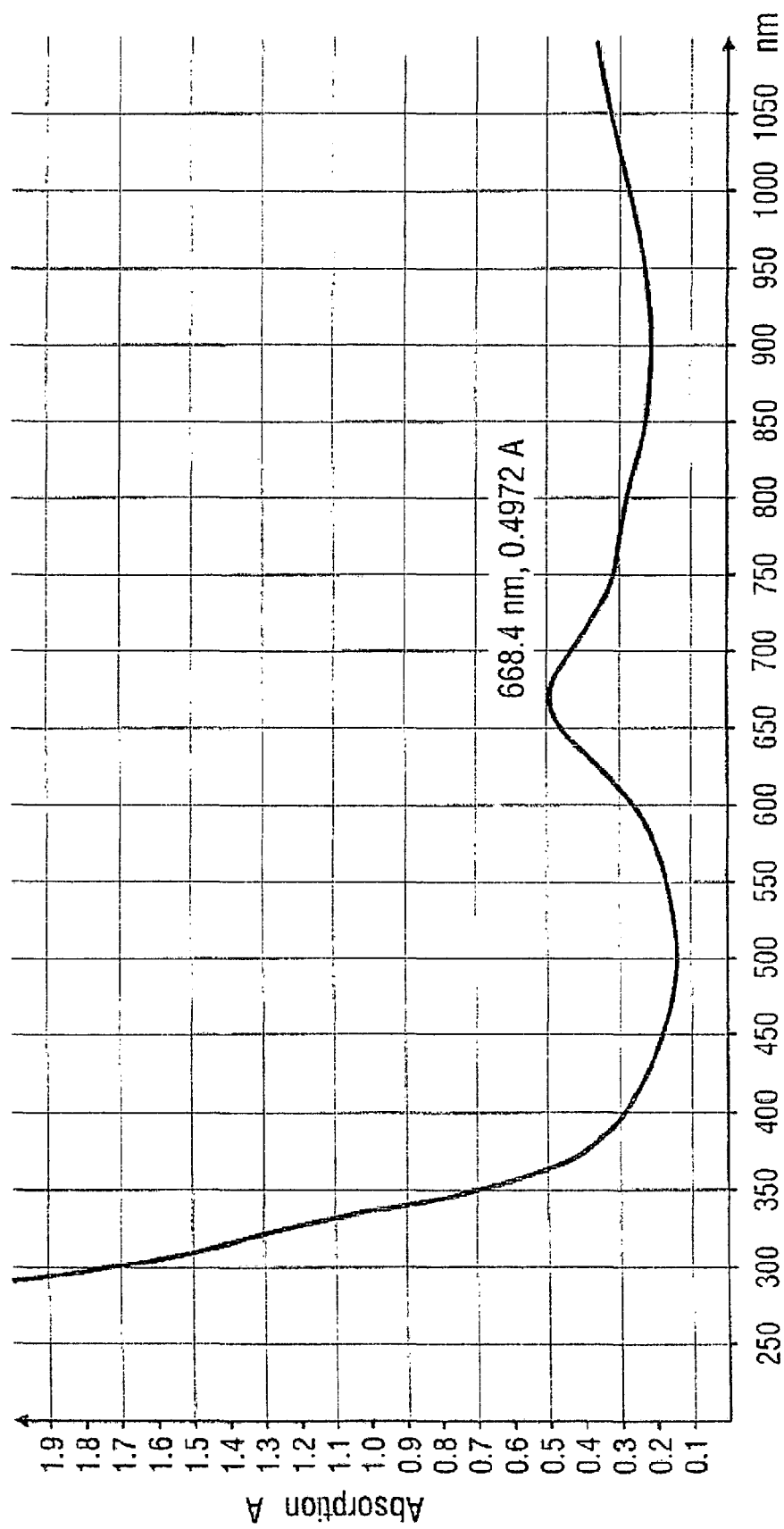
Fig. 2: Ultraviolet/visible spectrum of the compound obtained in the example 2 (51.9 mg/50 ml in DI water)

PROCESS FOR THE PREPARATION OF IRIDIUM ACETATE

The present invention relates to a process for the preparation of iridium acetate and to the iridium acetate obtainable according to that process. Additionally, the present invention relates to a process for the preparation of an iridium containing precipitate and applications of the precipitate and the iridium acetate (as a solid or in solution).

The present invention also relates to iridium acetate having a low halide content, as a solid or as a solution, an iridium containing precipitate having a low halide content and a process for the preparation of these products.

The invention also relates to the use of the iridium acetate having a low halide content of the present invention and of the corresponding iridium acetate solution as a catalyst or a catalyst precursor in homogeneously or heterogeneously catalyzed reactions, selected from the group consisting of carbonylation reactions, hydroformylation reactions, coupling reactions, oxidation reactions, hydrogenation reactions, and hydrosilylation reactions, in electroplating, or for the preparation of catalysts for heterogeneous catalysis.

A widespread application of iridium and compounds or complexes of iridium is their use as a catalyst for various chemical reactions, such as isomerization reactions, hydroformylation reactions or carbonylation reactions. Recently, particularly carbonylation reactions catalyzed by iridium or its compounds have gained in importance. One example is the iridium catalyzed carbonylation of methanol (with carbon monoxide) resulting in acetic acid or a reactive derivative thereof, referred to as Cativa process. Green iridium acetate was, inter alia, described as a suitable iridium compound for that process (EP-A-0 849 248).

Processes for the preparation of iridium carboxylates were already described in the past. For example, a process is known from WO-A-96/23757, in which at least one chloride or bromide compound of iridium is reacted with an alkali or alkaline earth carboxylate in a medium containing a carboxylic acid to give an iridium carboxylate containing solution. To be able to use the solution for catalytic purposes, the alkali and alkaline earth chlorides and bromides obtained with this process as byproducts of the reaction are separated using ion exchange columns, wherein the alkali metal or alkaline earth metal ions are separated using a cationic ion exchange resin and the chloride or bromide ions are separated using an anionic ion exchange resin.

The process yields iridium acetate solutions with chloride contents below 0.0020% by weight, wherein these values are based on the iridium containing solution. The described solutions, however, have iridium contents of 1.65% by weight Ir (example 2) and 0.62% by weight Ir (example 3), resulting in a content of 1212 and 3225 ppm chloride, respectively, based on the proportion of iridium. These chloride contents are still too high for certain applications in catalysis.

The process according to WO-A-96/23757 has the further disadvantage that the ion exchange materials required for the separation of chloride and bromide ions interfering with catalytic purposes are expensive. Furthermore, the process takes much time due to the time needed for the double ion exchange and the necessary regeneration of the column materials. Furthermore the ion exchange may lead to losses in yield.

From EP-A-1 046 629 a process for the preparation of iridium acetate is known, wherein iridium hydroxide is precipitated from an aqueous solution of an iridium chloro compound using an aqueous solution of an alkali metal hydroxide, carbonate or hydrogen carbonate, the precipitated iridium hydroxide is separated and reacted with acetic acid or a mixture of acetic anhydride to give an iridium acetate containing solution and the iridium acetate is isolated from the solution as a solid. To obtain iridium acetate with a low chloride content, the iridium hydroxide is preferably reprecipitated prior to the reaction with acetic acid. To this, the iridium hydroxide is dissolved with nitric acid or with a mixture of nitric acid and hydrogen peroxide and iridium hydroxide is reprecipitated from the formed solution by addition of an aqueous solution of an alkali metal hydroxide, carbonate or hydrogen carbonate. The iridium acetate isolated from the dark green solution is described as a dark green, glossy solid. The process, however, requires the isolation of the iridium acetate first obtained in aqueous solution as a solid, which is typically performed by evaporation optionally under vacuum. This isolation step is not only disadvantageous, because the evaporation of the aqueous solution takes a very long time (and therefore adversely affects the price of the product), but also bears the danger of decomposition or change of the product. Furthermore the reported yields leave room for improvement.

Furthermore, in the course of the studies leading to the present invention it turned out, that the iridium acetate, described in EP-A-1 046 629 as "being low in chloride content" without giving any exact values, still contains amounts of chloride impurities even after performing the reprecipitation recommended in that description to reduce the chloride content. The obtained amounts of chloride impurities are too high and thus need improvement particularly with regard to the desired application for catalytic purposes Based on these findings it was an object of the present invention to provide an inexpensive process for the preparation of iridium acetate, whereby iridium acetate can be obtained in high yield and in high purity.

Another object of the present invention was to provide iridium acetate having a low halide content and to provide an inexpensive process for the preparation thereof. Iridium acetate should be obtained in high yield and in high purity, particularly with a low halide content.

These objects have been achieved by the surprising finding that iridium acetate can be obtained in high yield and in high purity, when the process as defined in the claims, is conducted in the presence of at least one compound, selected from oxalic acid, a salt of oxalic acid, formic acid and a salt of formic acid (subsequently oxalic acid, a salt of oxalic acid, formic acid and a salt of formic acid are briefly referred to as "component (i)").

The present invention thus relates to a process for the preparation of iridium acetate comprising the steps of:
(a) reacting an iridium compound with an alkaline compound in a protic solvent to obtain an iridium containing precipitate, wherein the reaction is conducted in the presence of at least one compound selected from oxalic acid, a salt of oxalic acid, formic acid and a salt of formic acid, and
(b) reacting the precipitate, optionally after separation, in the presence of
   (i) at least one compound selected from oxalic acid, a salt of oxalic acid, formic acid and a salt of formic acid, and
   (ii) $CH_3CO_2H$ and/or $CH_3(CO)O(CO)CH_3$ (subsequently briefly referred to as component (ii))
   to give an iridium acetate containing solution, and
(c) optionally isolating the iridium acetate as a solid from the solution.

The present invention also relates to a process for the preparation of an iridium containing precipitate, the process comprising step (a) as defined above, and to the iridium containing precipitate obtainable according to that process.

Furthermore, the present invention relates to an iridium acetate having a halide content of less than 1000 ppm, preferably less than 800 ppm (based on Ir), which is obtainable, for example, by the process of the present invention. Additionally, the present invention relates to an iridium containing precipitate having a halide content of less than 1000 ppm and preferably less than 800 ppm (based on Ir), and which is obtainable, for example, as an intermediate in the process of the present invention.

Furthermore the present invention relates to the use of the iridium acetate of the present invention or of the iridium containing precipitate as a catalyst or a catalyst precursor in homogeneously or heterogeneously catalyzed reactions, selected from carbonylation reactions, hydroformylation reactions, coupling reactions, oxidation reactions, hydrogenation reactions, hydrosilylation reactions and isomerization reactions, and to the use in electroplating.

In the present invention the term "at least one compound selected from (the listed possibilities)" means that one compound from the listed possibilities is required to be present and more than one compound from the listed possibilities, i.e. for example a mixture of two or three or more of the listed possibilities, may be present.

The term "ammonium" in the present invention means a quaternary ammonium ion represented by the formula $[NR^1R^2R^3R^4]^+$, wherein $R^1, R^2, R^3$, and $R^4$ are independently selected from a hydrogen atom and a lower alkyl group (preferably a $C_1$ to $C_6$ alkyl group), that may be linear, branched or cyclic. Preferably at least one of $R^1$ to $R^4$ represents a hydrogen atom and particularly preferably all of $R^1$ to $R^4$ represent a hydrogen atom.

In the present invention the term "iridium acetate" means a compound having iridium atom(s) and acetate and is to be understood in this broad sense.

The term "protic solvent" in the present invention means a solvent containing or able to release protons and/or able to form hydrogen bonds. Examples of protic solvents useful in the present invention are water and alcohols, e.g. $C_1$-$C_6$ alkanols (preferably methanol, ethanol, n-propanol, iso-propanol, n-butanol, sec-butanol, tert-butanol), and mixtures of two or more of these solvents. Preferred protic solvents for the purposes of the present invention are water and a mixture of water and a $C_1$-$C_6$ alkanol (preferably methanol). However, the present invention is not limited to these specific solvents. Suitable mixing ratios can readily be determined by one of ordinary skill in the art.

In the present invention the term "inert gas" means a gaseous atmosphere, which is inert towards the starting compounds, the reaction mixture or the reaction products, respectively, i.e. will neither chemically nor physically alter them. Specifically the inert gas used is preferably essentially free of oxygen. Inert gases suitable for the purposes of the present invention include, but are not limited to for example nitrogen, argon or other noble gases and mixtures thereof. Herein, the term "essentially free of oxygen" means, that the amount of oxygen that might be present in the inert gas atmosphere is in a range that does not adversely affect the course of the reaction, the yield and purity of the intermediates and end products.

The amount of oxygen in the inert gas atmosphere that is still acceptable for the purposes of the present invention is about 2 percent by volume. Typically, the amount of oxygen in the inert gas atmosphere is less than about 1000 ppm, more preferably less than about 500 ppm (in terms of ideal volume fractions, i.e. parts by moles).

This can be achieved, for example, by using industrial inert gases having a purity of about 99.99% by volume. The amount of oxygen contained in the inert gas used may for example be, but is not limited to, less than about 100 ppm.

In the following the process of the present invention will be described: The steps (a) and (b) will be described in detail.

Step (a)

Step (a) comprises reacting an iridium compound with an alkaline compound in a protic solvent to obtain an iridium containing precipitate. According to the present invention the reaction is conducted in the presence of at least one compound, selected from oxalic acid, a salt of oxalic acid, formic acid and a salt of formic acid (component (i)).

The salts of oxalic acid and the salts of formic acid are not particularly limited. Basically, any salt of oxalic acid or formic acid may be used. Usually, the salt will be selected so that it is soluble in the protic solvent under the chosen reaction conditions.

Suitable oxalic acid salts include, but are not limited to, ammonium salts, alkali salts (i.e. lithium, sodium, potassium and cesium salts) and alkaline earth salts (i.e. magnesium, calcium, barium and strontium salts) of oxalic acid. Preferred examples include the sodium salt, the magnesium salt and ammonium salts of oxalic acid.

Suitable formic acid salts include, but are not limited to, ammonium salts, alkali salts (i.e. lithium, sodium, potassium and cesium salts) and alkaline earth salts (i.e. magnesium, calcium, barium and strontium salts) of formic acid. Preferred examples include the sodium salt, the calcium salt and ammonium salts of formic acid.

For performing of step (a) either one single compound, selected from component (i), or a mixture of several compounds, selected from component (i), may be used.

In a preferred embodiment, step (a) is conducted in the presence of oxalic acid and/or ammonium oxalate.

The iridium compound used as a starting material is not particularly limited. Thus the term "iridium compound", as used herein, is to be interpreted in a broad sense and includes both stoichiometric and non-stoichiometric compounds of iridium. The iridium compounds may also be complex-like compounds of iridium.

In the practice of the invention it has proven useful to use an iridium compound as a starting material, that can be dissolved in the protic solvent used for the reaction.

The oxidation state of the iridium in the iridium compound is not limited. Preferably the iridium is present in the oxidation state (0), (+I), (+III) or (+IV), preferably (+III) or (+IV), particularly preferably in the oxidation state (+IV). It is also possible for the iridium compound used as a starting material to contain iridium in a first oxidation state as well as iridium in a second (different from the first) oxidation state, for example iridium in the oxidation state (+III) as well as in the oxidation state (+IV). As examples of such iridium compounds mixed iridium(III)/iridium(IV) halides and their hydrates can be mentioned.

From an economical viewpoint the use of readily available, e.g. commercially available, and inexpensive iridium compounds is preferred.

In a preferred embodiment the iridium compound is selected from iridium halogen (i.e. chlorine, bromine, or iodine, preferably chlorine) compounds, including but not limited to iridium(III) chloride, iridium(III) bromide, iridium(III) iodide, iridium(III) chloride hydrate, iridium(III) bromide hydrate, iridium(III) iodide hydrate, iridium(IV) chloride, iridium(IV) bromide, iridium(IV) iodide, iridium(IV) chloride hydrate, iridium(IV) bromide hydrate, iridium(IV) iodide hydrate, iridium(III)/iridium(IV) chloride, iridium (III)/iridium(IV) bromide, iridium(III)/iridium(IV) iodide, iridium(III)/iridium(IV) chloride hydrate, iridium(III)/iridium(IV) bromide hydrate, iridium(III)/iridium(IV) iodide hydrate, hexachloroiridium(III) acid and its ammonium, alkali (preferably sodium and potassium) and alkaline earth (preferably magnesium and calcium) salts, hexabromoiridium(III) acid and its ammonium, alkali (preferably sodium and potassium) and alkaline earth (preferably magnesium and calcium) salts, hexachloroiridium(IV) acid and its ammonium, alkali (preferably sodium and potassium) and alkaline earth (preferably magnesium and calcium) salts, hexabromoiridium(IV) acid and its ammonium, alkali (preferably sodium and potassium) and alkaline earth (preferably magnesium and calcium) salts. Also suitable are amine chloro complexes of the formula $[IrCl_n(NH_3)_{6-n}]^{(3-n)+}$ optionally having one or more counter ions for charge equalization (e.g. alkali, alkaline earth, or chloride ions), wherein n is an integer of 1 to 5, or compounds, such as $[Ir(CO)_2Cl]_2$, $Ir_4(CO)_{12}$ or $Ir(acac)_3$.

With respect to the solubility in the protic solvent used and from an economical viewpoint the use of hexachloroiridium (III) acid and its sodium, potassium and ammonium salts, hexachloroiridium(IV) acid and its sodium, potassium and ammonium salts and of mixed iridium(III)/iridium(IV) halides and hydrates thereof is preferred. The use of $Na_2IrCl_6$, $K_2IrCl_6$, $(NH_4)_2IrCl_6$, $H_2IrCl_6$, $Na_3IrCl_6$, $K_3IrCl_6$, $(NH_4)_3IrCl_6$, $H_3IrCl_6$ and iridium(+III)/iridium(+IV) chloride (hydrate) is particularly preferred.

A mixture of two or more different iridium compounds may also be used.

Examples of protic solvents useful in step (a) of the present invention are water and alcohols, e.g. $C_1$-$C_6$ alkanols (preferably methanol, ethanol, n-propanol, iso-propanol, n-butanol, sec-butanol, tert-butanol), and mixtures of two or more of these solvents. Preferably water or a mixture of water and a $C_1$-$C_6$ alkanol (preferably methanol) is used as a protic solvent.

The alkaline compound is selected from substances, the solutions of which exhibit an alkaline reaction in the presence of the protic solvent used. Examples of alkaline compounds suitable in the present invention are hydroxides of ammonium, alkali metals (i.e. Li, Na, K, Rb, Cs) or alkaline earth metals (i.e. Mg, Ca, Ba, Sr), carbonates and hydrogen carbonates of ammonium, alkali metals (i.e. Li, Na, K, Cs) or alkaline earth metals (i.e. Mg, Ca, Ba, Sr) or amines of the formula $NR^1R^2R^3$, wherein $R^1$, $R^2$ and $R^3$ are independently selected from a hydrogen atom and $C_1$-$C_6$ alkyl groups (such as ammonia, triethyl amine and trimethyl amine). As the alkaline compound preferably an alkali metal hydroxide is used, more preferably sodium hydroxide or potassium hydroxide and most preferably potassium hydroxide is used. A mixture of two or more alkaline compounds may also be used.

The alkaline compound may be used as such or dissolved in one or more protic solvent(s), as defined above. Preferably the alkaline compound is at least partially dissolved in the protic solvent (mixture).

To generate a precipitate it has proven advantageous to use the alkaline compound as solution in a protic solvent (preferably water) in a concentration of at least 1% by weight, preferably at least 5% by weight, more preferably in a concentration of 10 to 30% by weight, based on the protic solvent used.

The alkaline compound is preferably used in an amount, based on iridium, significantly higher than the stoichiometric amount. The ratio of the alkaline compound (in moles, based on a monohydric alkaline compound) to iridium (moles) may for example be more than 2, preferably 3 to 20, particularly preferably 7 to 14. A suitable amount of the iridium compound is e.g. 0.5 to 15% by weight, preferably 1 to 8% by weight, particularly preferably 1.5 to 5% by weight, based on the starting solution used.

The compound selected from component (i) is preferably used in at least an about equimolar amount (e.g. at least 0.8 mol equivalents, more preferably at least 1.0 mol equivalent, even more preferably 1.05 to 1.5 mol equivalents, based on iridium). When a mixture of compounds of the component (i) is used, the amounts shown refer to the total number of moles of the selected compounds.

Step (a) is preferably conducted in an atmosphere of inert gas. Hence in a preferred embodiment both the reaction apparatus and the reactants used are rendered oxygen free by purging with an inert gas in a per se known manner.

To obtain an iridium containing precipitate having good filtration properties step (a) is preferably conducted at a pH of about 6 to about 10, preferably of about 7 to about 9, particularly preferably at a pH of about 7.5.

It has also proven advantageous to conduct step (a) with heating for example at 50 to 120° C., particularly 60 to 110° C., more preferably 70 to 95° C. If step (a) is conducted with heating, it is preferable to cool or allow to cool the reaction mixture to room temperature prior to performing step (b).

The addition of the iridium compound, of the alkaline compound, of said at least one compound selected from component (i) and of the protic solvent may be performed in any order. For example, first the protic solvent may be added and the iridium compound, the alkaline compound and the compound selected from component (i) may be added in any order or simultaneously.

Although the addition of the iridium compound and of the alkaline compound may be performed in any order, it may be advantageous to first form a mixture (preferably solution) comprising the iridium compound and at least one compound selected from component (i) in the protic solvent.

Accordingly, in a preferred embodiment of the invention step (a) comprises the substeps (a1) and (a2). In the present invention every reference to step (a) is to be understood as well as a reference to the preferred embodiment comprising the substeps (a1) and (a2), unless stated otherwise.

Substep (a1)

Substep (a1) comprises forming a mixture (preferably solution) comprising the iridium compound and at least one compound selected from component (i), and the protic solvent optionally with heating.

The addition in substep (a1) may be performed in any order. For example first a mixture (preferably solution) comprising the iridium compound and a protic solvent, each defined as above, may be formed, to which at least one compound selected from component (i), optionally dissolved in a protic solvent, is added. The opposite order is acceptable as well. The addition may be performed independently from the order under the conditions subsequently defined for step (a).

Substep (a1) is preferably performed with heating for example at 50 to 120° C., particularly 60 to 110° C., more preferably 70 to 95° C. Particularly preferably, the elevated temperature in step (a1) is maintained for a prolonged period of time, for example for a period of several minutes, particularly more than 10 minutes, preferably more than 30 minutes, even more preferably about 45 minutes to 3 hours.

Substep (a1) is preferably conducted in an atmosphere of inert gas.

Substep (a2)

Substep (a2) comprises reacting the mixture (preferably solution) obtained in step (a1) with the alkaline compound (as defined above) to obtain an iridium containing precipitate, optionally with heating.

The addition in substep (a2) may be performed in any order. For example, first the mixture (preferably solution) obtained in substep (a1) may be added and the alkaline compound, optionally dissolved in a protic solvent, can be added thereto, or, conversely, first a mixture (preferably solution) comprising the alkaline compound and a protic solvent, each as defined above, may be formed, to which the mixture obtained in substep (a1) is added.

In a preferred embodiment substep (a2) is performed such that first the mixture (preferably solution) obtained in substep (a1) is prepared and a solution comprising the alkaline compound and the protic solvent is added.

Substep (a2) is preferably performed with heating for example at about 50 to about 120° C., preferably about 60 to about 110° C., more preferably about 80 to about 95° C. Particularly preferably the elevated temperature in substep (a2) is maintained for a prolonged period of time, for example for a period of several hours, particularly more than 10 hours, preferably more than 15 hours, even more preferably more than 30 hours. The reaction time has no upper limit, but is typically less than 100 hours, preferably less than 90 hours, particularly preferably less than 80 hours. Most preferably, the reaction time is approximately 40 hours.

Substep (a2) is preferably conducted in an atmosphere of inert gas.

Independently from the order of the addition of the iridium compound, the alkaline compound and the compound selected from component (i), the addition in step (a) and substeps (a1) and (a2) is typically performed with stirring. Independently from the order of the addition the addition may be performed for example by adding one single portion (i.e. as fast as possible) or by adding the substances to be added dropwise or in small amounts respectively over a period of a few seconds to several hours, e.g. within 10 seconds to 3 hours, preferably within 1 minute to 60 minutes.

In one embodiment of the invention the pH of the reaction mixture is adjusted to a value of about 6 to about 9, preferably to about 7 to about 8.5, after completion of step (a) (i.e. after obtaining an iridium containing precipitate) and prior to performing step (b). The pH may be adjusted by adding either an additional amount of the alkaline compound, as defined above, or by adding a weakly acidic compound, such as diluted acetic acid or hydrochloric acid and mixtures thereof.

To keep the halide content small for a later use as a catalyst, the pH is preferably not adjusted with an acid, that may additionally introduce halide ions into the reaction mixture.

In the practice of the invention, acetic acid in a concentration of about 0.5 to 100% by weight, preferably 35 to 65% by weight, particularly preferably about 50% by weight (in water) has proven useful as a means to adjust the pH.

Step (a) may comprise one or more optional substeps selected from separating, washing and reprecipitating the obtained iridium containing precipitate.

Particularly when a halide containing iridium compound is used, carrying-out of separating and washing the iridium containing precipitate may advantageously affect the halide content of both the iridium containing precipitate and the iridium acetate obtainable therefrom. Particularly for a later application as a catalyst or catalyst component for homogeneously or heterogeneously catalyzed reactions the halide content should be as low as possible.

Suitable conditions for the optional separation and the optional washing of the precipitate may be determined by one of ordinary skill in the art by routine tests. The following conditions are therefore not to be construed as limiting the invention.

The optional separation of the obtained precipitate may be conducted by operations such as filtration, suction filtration, sedimentation or centrifugation. When separating the precipitate it may prove advantageous to avoid complete drying of the precipitate.

The optional washing step of the precipitate may be conducted for example with a suitable washing liquid. As a washing liquid any liquid may be used, that is inert towards the precipitate of iridium hydroxide, i.e. that neither reacts with nor dissolves the same. Suitable washing liquids are for example water, acetic acid, hydrochloric acid and mixtures thereof.

To avoid the introduction of halide ions into the precipitate, however, halide free washing liquids, such as water and acetic acid and mixtures thereof (e.g. 5 to 20% by weight acetic acid, particularly preferably 8 to 12% by weight acetic acid) are preferably used as washing liquids. In cases though, where the halide content is not critical, a halide containing washing liquid, such as hydrochloric acid diluted with water, may also be used. The washing liquid may optionally be slightly heated, e.g. at a temperature between 25 and 65° C., preferably 40 to 60° C. (e.g. about 50° C.).

In a preferred embodiment of the invention step (a) comprises the step of separating and washing the iridium containing precipitate. Particularly preferably, the precipitate is repeatedly washed, until halide ions (specifically chloride ions) can no longer be detected in the filtrate. The detection of halide ions in the filtrate can be performed in a manner known to the skilled person, for example using silver ions.

The detection of chloride ions as silver chloride precipitate is very sensitive. With the naked eye chloride ions down to an amount of 50 ppm can be detected, i.e. the absence of turbidity when adding silver ions typically indicates a chloride content of less than about 50 ppm.

Reprecipitation may optionally be conducted by dissolving the iridium containing precipitate in a suitable solvent and again precipitating with the alkaline compound (as described above). As solvents e.g. organic (e.g. acetic acid) or inorganic acids (e.g. hydrochloric acid, nitric acid) optionally in admixture with a protic solvent, as defined above, may be used.

When desired, the reprecipitation may also be conducted in the presence of at least one compound selected from component (i). This is preferred. The reprecipitation step may optionally be conducted once or several times (e.g. twice, thrice). Preferably, the reprecipitation step(s) is (are) conducted in an atmosphere of inert gas (as described above).

Typically, precipitates are obtained in step (a), that surprisingly even without conducting any reprecipitation step exhibit a high purity, as subsequently described in detail with regard to the obtained precipitate. Thus, a more preferred embodiment does not include a reprecipitation step of the iridium containing precipitate.

The optional steps of separating, washing and reprecipitating the precipitate are preferably conducted in an atmosphere of inert gas.

The iridium containing precipitate obtained in step (a) may be obtained in very good yields of typically about 92 to 95% or more, based on iridium (i.e. moles Ir (educt)/moles Ir (product)).

In one embodiment, step (a) comprises a step of allowing the iridium containing precipitate to age. The term "ageing" is known in the art and means a change in the physical and/or chemical properties of a substance during storage. The changes may occur naturally (e.g. by action of the ambient conditions on the substance) or may be generated artificially, e.g. by action of elevated temperature.

In the present invention, however, it is not preferred to allow the iridium containing precipitate to age. Rather, a freshly precipitated iridium containing precipitate is preferably used for further reaction (e.g. the reaction in step (b)). The term "freshly precipitated" is to be understood in such a way, that the exposure to conditions causing a change in chemical and physical properties of the precipitate (i.e. allowing the precipitate to age) is preferably prevented. Such conditions may for example be one or more conditions selected from allowing to stand for a prolonged period of time (e.g. several hours, particularly more than 3 hours), action of oxygen (for example in the form of air), removal of the protic solvent, removal of hydrate water and the like.

In a particularly preferred embodiment one or more conditions selected from allowing to stand for more than 3 hours (particularly for more than 2 hours, more preferably for more than 1 hour, even more preferably for more than 30 minutes) at room temperature in an atmosphere of inert gas, action of oxygen (e.g. in the form of air, particularly for more than 30 minutes) and complete drying are avoided. In this preferred embodiment the term freshly precipitated refers to the precipitate obtained under such condition(s).

In this embodiment the precipitate obtained in step (a) is optionally reprecipitated, optionally separated and optionally washed, as described above, and immediately used for the desired application, e.g. for the reaction in step (b). The precipitate is preferably used for the desired application within a period of time of less than 3 hours, more preferably within a period of time of 2 hours, even more preferably within a period of time of 1 hour and most preferably within a period of time of 30 minutes, measured from the time of separation from the reaction mixture.

Step (b)

Step (b) comprises the reaction of the iridium containing precipitate obtained in step (a) to give an iridium acetate containing solution.

According to the present invention step (b) is conducted in the presence of at least one compound selected from oxalic acid, a salt of oxalic acid, formic acid and a salt of formic acid (i.e. component (i)) and in the presence of at least one compound selected from (ii) acetic acid ($CH_3CO_2H$) and/or acetic acid anhydride ($CH_3(CO)O(CO)CH_3$) (i.e. component (ii)).

The salts of oxalic acid and formic acid are not particularly limited. Basically, any salt of oxalic acid and any salt of formic acid may be used in step (b). Usually, the salt will be selected so that it is soluble in the reaction mixture under the chosen reaction conditions. Suitable examples of the salts of oxalic acid and suitable examples of the salts of formic acid include but are not limited to the compounds exemplified for step (a).

The compound(s) selected from component (i) used in step (b) may be the same compound(s) as in step (a). Alternatively, different compounds or different mixtures of compounds selected from component (i) may be used in steps (a) and (b).

Step (b) is preferably conducted in the presence of formic acid or a salt thereof.

According to the present invention step (b) is conducted in the presence of at least one compound selected from $CH_3CO_2H$ and/or $CH_3(CO)O(CO)CH_3$ (component (ii)). Preferably, step (b) is conducted in the presence of $CH_3CO_2H$ or in the presence of a mixture of $CH_3CO_2H$ and $CH_3(CO)O(CO)CH_3$, particularly preferably in the presence of $CH_3CO_2H$.

Component (ii) may be provided for the reaction in step (b) in any form. For example, component (ii) may be present as such as well as in the form of a mixture with one or more protic solvents. In a preferred embodiment component (ii) is used as such, i.e. without addition of a protic solvent. Suitable protic solvents include the examples listed in step (a), with water being preferred as protic solvent. The mixing ratio of component (ii) and the protic solvent may be in the range of 99:1 to 1:99. As an example of one such mixture e.g. a mixture of glacial acetic acid and water in a ratio of 10:90 to 50:50, in terms of volume parts, may be illustrated. If component (ii) is provided as mixture with a protic solvent (mixture), the protic solvents used in steps (a) and (b) may be the same or different. Preferably in both steps the same protic solvent (mixture) is used. The use of component (ii) in the form of a mixture with a protic solvent selected from water and a $C_1$-$C_6$ alkanol, as defined in step (a), has proven useful.

In a particularly preferred embodiment step (b) is conducted in the presence of 100% by weight to 95% by weight acetic acid (in water).

In step (b) the at least one compound selected from component (i) is preferably used in at least an about equimolar amount (e.g. at least 0.8 mol equivalents, more preferably at least 1.0 mol equivalent, even more preferably 1.05 to 1.5 mol equivalents, based on iridium). When a mixture of compounds of component (i) is used, the amounts shown refer to the total number of moles of the selected compounds.

In step (b) the least one compound selected from component (ii) is used in a molar ratio of the compound selected from component (ii) to iridium, that is significantly higher than the stoichiometric ratio. Thus the at least one compound selected from component (ii) may serve both as a reactant and as a solvent for the resulting iridium acetate.

In the course of the reaction in step (b) the reaction mixture is converted from a suspension of the iridium containing precipitate to a solution of iridium acetate.

Accordingly, the reaction time for step (b) is chosen so that at the end of the reaction time an essentially clear solution containing no substantial (preferably no visible) amounts of solids is formed. Preferred reaction times for step (b) are about 8 to about 50 hours, preferably about 10 to about 25 hours, more preferably about 12 to about 17 hours.

In a preferred embodiment step (b) is conducted with heating e.g. at a temperature ranging from about 80 to 120° C., particularly preferably from about 90 to 105° C.

It is particularly preferred to perform step (b) with heating to reflux. The exact temperature will mainly depend upon the compound selected from component (ii), that will be used. Typically a suitable temperature will be more than about 100° C., e.g. about 101 to about 112° C. for 60% by weight acetic acid in water, about 118° C. for 100% by weight acetic acid (glacial acetic acid) and about 139° C. for 100% by weight acetic anhydride.

Step (b) is preferably conducted in an atmosphere of inert gas.

Optionally, the solution obtained in step (b) comprising iridium acetate may be filtered to remove any insoluble residues possibly contained in the solution. However, usually no visible residue is seen on the filter, which is indicative for the completeness of the reaction in step (b). The optional filtering step may be performed by means known to one of ordinary skill in the art, e.g. by filtering through various filters (e.g.

Blauband, or membrane) or/and polishing filtration through various filters (e.g. nylon filters having a pore size of preferably more than 5 μm to 20 μm).

The filtration may also be performed under pressure, for example under pressures between 1 and 5 bar, preferably at about 2 bar. The filtration may be performed at any temperature, e.g. at a temperature ranging from 20 to 30° C. The filtration may be performed in the absence or presence of filtering aids, such as glass frost, activated carbon, cellulose (e.g. Hyflow). The filtration is preferably conducted in an atmosphere of inert gas.

If step (b) is conducted with heating, it is preferable to cool or allow to cool the solution to room temperature prior to performing optional steps, such as filtration or step (c).

Step (c)

If desired the iridium acetate may be isolated from the solution as a solid. The separation may be performed in a per se known manner, e.g. by concentrating the reaction mixture or distilling off the volatile components contained in the reaction mixture optionally under vacuum and/or at elevated temperatures. However, the present invention is not limited to these illustrated methods of isolation. Step (c) may be conducted in an atmosphere of inert gas, however, this is neither required nor preferred.

In the process of the present invention iridium acetate can be produced in very good yields (about 95% or more, based on Iridium (in moles) and with respect of the entire process).

Additionally the iridium acetate of the present invention is characterized by its high purity, as described in the following in more detail.

Iridium Acetate

In one embodiment, the present invention relates to iridium acetate obtainable according to the process as described in any of claims 18 to 22.

After conducting the steps (a) and (b) of the present invention a solution containing iridium acetate is obtained. In one embodiment, the present invention relates to a such a solution containing iridium acetate.

As described above, iridium acetate may also be isolated from the solution as a solid, if desired. In another embodiment, the present invention relates to iridium acetate as a solid.

Hence, according to the present invention, the iridium acetate of the present invention may be present as a solid or dissolved in a suitable solvent. Suitable solvents include, but are not limited to protic solvents. Suitable protic solvents are, for example, water and alcohols, e.g. $C_1$-$C_6$ alkanols (preferably methanol, ethanol, n-propanol, iso-propanol, n-butanol, sec-butanol, tert-butanol), and mixtures of two or more of these solvents. If the iridium acetate is present as a solution this solution is not limited with regard to its composition.

A preferred solution comprises (preferably consists of), in addition to the iridium acetate of the present invention, at least one compound selected from component (i), and at least one compound selected from component (ii), and, optionally, a protic solvent (mixture). This preferred solution is not limited with regard to its composition.

In a more preferred embodiment the iridium acetate solution comprises (preferably consists of) the following components:
2 to 20% by weight of iridium acetate,
20 to 90% by weight of component (ii) (preferably acetic acid), 1 to 20% by weight of component (i) (preferably formic acid), and
5 to 70% by weight of a protic solvent (mixture) (preferably water).

The iridium acetate of the present invention (as a solid and as a solution) is characterized by its low content of impurities. Such impurities may for example be ionic constituents contained in the starting compounds used, such as ammonium, alkali or alkaline earth ions or halide ions.

The iridium acetate of the present invention is in the form of a solution as well as in form of the isolated solid stable towards air and may be stored for a prolonged period of time (e.g. for a period of several months to 2 years) without any change in the physical and chemical properties.

Moreover, the iridium acetate present as a solid is characterized by its very good solubility in solvents, such as water, acetic acid ($CH_3COOH$) and methanol, and mixtures of one or more of these solvents.

Typically, the iridium acetate of the present invention (as solid and as a solution) is blue-green in color, whereas prior art consistently reports "green iridium acetate". In all examples of EP-A-01 046 629 a dark green solution or suspension of iridium acetate is obtained, from which a dark green solid is obtained by evaporation. The solution of iridium acetate obtained in example 1 of WO-A-96/23757 is also described as being "green".

FIG. 1 shows a visible/ultraviolet spectrum of the compound obtained in comparative example 1 (according to EP-A-01 046 629).

FIG. 2 shows a visible/ultraviolet spectrum of iridium acetate according to the present invention.

A comparison of the spectra shown in FIG. 1 and FIG. 2 shows that the absorption maximum ($\lambda_{max}$) of the iridium acetate of the present invention is shifted towards shorter wavelengths, as compared to the iridium acetate obtained according to the process of EP-A-01 046 629. This indicates a specific chemical structure of the iridium acetate of the present invention. Generally, the absorption maximum ($\lambda_{max}$) of the iridium acetate of the present invention is shifted to wavelengths shorter than 680 nm, preferably shorter than 675 nm and more preferably shorter than 670 nm in the visible/ultraviolet spectrum.

In another aspect, the present invention relates to an iridium acetate (as a solid or as a solution, as described above) characterized in having a low halide (preferably chloride) content. In particular, the iridium acetate of the present invention is characterized by having a very low halide (preferably chloride) content of less than 1000 ppm, and more preferably less than 800 ppm (all ppm values in terms of parts by weight, based on Ir)

In particularly preferred embodiments of the invention, as described above, halide contents below 200 ppm, particularly below 100 ppm or even lower, e.g. below 50 ppm, are obtained (all ppm values in terms of ppm by weight, based on Ir).

The content of other impurities (particularly ammonium, alkali or alkaline earth ions) is in the same order of magnitude as the results obtained for the halide impurities.

In preferred embodiments, the contents of other impurities, particularly ammonium, alkali (i.e. Li, Na, K, Rb, Cs, preferably K) or alkaline earth (i.e. Mg, Ca, Ba, Sr, preferably Mg and Ca) ions each are typically below 1000 ppm, preferably below 500 ppm and particularly preferably below 300 ppm (based on Ir).

The halide content (which in this application is understood as being the total halide content, comprising the ionically as well as the covalently bound halide of the sample) may be determined using methods known to one of ordinary skill in the art. In the present invention a preferably used method of the determination (in the intermediate and in the end product) is the so called "analysis of total halide content according to WICKBOLD", as described in the examples.

The determination of the content of other possible ionic constituents (in the intermediate and in the end product) (such as ammonium, alkali or alkaline earth ions) is also known to one of ordinary skill in the art and, for example, ICP analysis (ICP=Inductive Coupled Plasma) may be used.

In a preferred embodiment, the iridium acetate with a low halide content of the present invention can be obtained by the processes defined in any of claims 18 to 22.

Iridium Containing Precipitate

In another aspect, the present invention also relates to an iridium containing precipitate.

The term "iridium containing precipitate", as used herein, refers to the iridium containing precipitate obtainable in step (a) from the iridium compound by adding the alkaline compound (i.e. in the presence of OH$^-$-ions) and is to be understood in this broad sense.

Without wishing to be bound by any specific theory it is believed that the precipitate is an iridium oxygen compound having besides the iridium atoms as compound constituents one or more compound constituents, selected from hydroxo, oxo and aquo groups and hydrate constituents, wherein the iridium atoms may be present in only one oxidation state (e.g. all in (+III) corresponding to Ir(III) oxide hydrate, or all in (+IV) corresponding to Ir(IV) oxide hydrate) or the iridium atoms may be present in oxidation states differing from one another, e.g. a portion in the oxidation state (+III) and the remainder in the oxidation state (+IV). Anyone skilled in the art of transition metal oxygen compounds knows that typically such compounds are non stoichiometric compounds.

In a preferred embodiment the term "iridium containing precipitate" refers to the freshly precipitated precipitate, as described above.

The iridium containing precipitate obtainable by conducting step (a) is characterized by a good filterability.

Additionally, it was surprisingly found that by conducting step (a) in the presence of at least one compound selected from component (i) a precipitate may be obtained, that is characterized by a very good solubility for example in inorganic acids, such as mineral acid (e.g. hydrochloric acid or nitric acid), and organic acids, such as acetic acid (or acetic anhydride).

Typically, the precipitate can be completely (typically more than 95% by weight) dissolved in the aforesaid acids or a mixture thereof. The role that the presence of component (i) plays is still unclear, however, it seems to cause the good solubility. The very good solubility of the iridium containing precipitate according to the present invention also means an improvement of the yield and hence of the productivity of the process for the preparation of iridium acetate. By minimizing the insoluble impurities the purity and stability of the iridium acetate obtained in step (b) is improved significantly.

In one embodiment the iridium containing precipitate is obtainable by the process according to any of claims 9 to 17.

According to the present invention, the iridium containing precipitate of the present invention is characterized in particular by its low content of impurities.

Such impurities may for example be ionic constituents contained in the starting compounds used, such as ammonium, alkali or alkaline earth ions or halide ions. For a later use as a catalyst or catalyst precursor, particularly the presence of halide ions (e.g. chloride, bromide or iodide ions, particularly chloride ions) is undesirable.

Hence, in a preferred embodiment the invention relates to an iridium containing precipitate having a low halide (preferably chloride) content.

The iridium containing precipitate of the present invention is characterized by a very low halide content (particularly chloride content). Typically the halide content is below 1000 ppm and more preferably below 800 ppm (based on Ir).

In particularly preferred embodiments of the invention, as described above, halide contents below 200 ppm, particularly below 100 ppm or even lower, e.g. below 50 ppm, are typically obtained. The given ppm values are based on iridium (in terms of parts by weight).

The precipitate is characterized by a very high purity in other respects as well. The content of other impurities is in the same order of magnitude as the results obtained for the halide impurities. Such other impurities may for example be ionic constituents contained in the starting compounds used, such as ammonium, alkali or alkaline earth ions.

The content of other impurities, particularly ammonium, alkali (i.e. Li, Na, K, Rb, Cs, preferably K) or alkaline earth (i.e. Mg, Ca, Ba, Sr, preferably Mg and Ca) ions is typically below 1000 ppm, preferably below 500 ppm and particularly preferably below 300 ppm (based on Ir).

The iridium containing precipitate having a low total halide content of the present invention can, for example, be obtained as an intermediate by the process as described in any of claims 9 to 17.

Surprisingly, these high degrees of purity in the products and intermediates of the present invention are obtained even when, as preferred in the present invention, troublesome means to reduce undesired impurities (particularly halide), as taught in the prior art (such as reprecipitation of the iridium containing precipitate e.g. by dissolving in nitric acid or a mixture of nitric acid and hydrogen peroxide and again precipitating by adding an alkali metal hydroxide, carbonate or hydrogen carbonate according to EP-A-1046629), are omitted.

The fact that the products and intermediates of the process of the present invention (i.e., iridium acetate and iridium containing precipitate) obtainable in absence of a reprecipitation step, according to a preferred embodiment of the invention, has even lower halide content than the iridium product obtainable according to the prior art process including such reprecipitation step (here a halide content of about 6% is obtained, in terms of % by weight based on Ir) is particularly surprising.

Uses

The present invention also relates to the use of the iridium acetate of the present invention (as a solid or in solution) and to the use of the iridium containing precipitate of the present invention as a catalyst or as a catalyst precursor in homogeneously or heterogeneously catalyzed reactions.

Preferably, the catalyzed reactions are reactions, selected from the group consisting of carbonylation reactions, hydroformylation reactions, coupling reactions, oxidation reactions, hydrogenation reactions, hydrosilylation reactions and isomerization reactions, preferably carbonylation reactions.

A particularly preferred embodiment relates to the use as a catalyst or as a catalyst precursor in homogeneously catalyzed reactions, particularly carbonylation reactions. Preferred carbonylation reactions include the carbonylation of methanol into acetic acid.

The iridium acetate of the present invention (as a solid or in solution) and the iridium containing solid of the present invention may also be used in electroplating and for the preparation of catalysts for heterogeneous catalysis.

In preferred embodiments, the present invention relates to the following items:

1. A process for the preparation of an iridium containing precipitate, the process comprising:
   (a) reacting an iridium compound with an alkaline compound in a protic solvent to obtain an iridium containing precipitate, wherein the reaction is conducted in the presence of at least one compound selected from oxalic acid, a salt of oxalic acid, formic acid and a salt of formic acid.
2. The process according to item 1, wherein the iridium compound is an iridium halogen compound.
3. The process according to item 1 or 2, wherein step (a) comprises separating the obtained precipitate from the reaction mixture.
4. The process according to item 3, further comprising washing of the separated precipitate.
5. The process according to item 4, wherein washing is conducted until the washing liquid is free of halide ions.
6. The process according to any one of items 1 to 5, wherein the reaction in step (a) is conducted with heating.
7. The process according to any one of items 1 to 6, wherein the alkaline compound is selected from ammonium, alkali and alkaline earth hydroxides, carbonates and hydrogen carbonates and amines of the formula $NR^1R^2R^3$, wherein $R^1$, $R^2$ and $R^3$ are independently selected from a hydrogen atom and $C_1$-$C_6$ alkyl groups, and mixtures thereof.
8. A process for the preparation of iridium acetate comprising the steps of:
   (a) reacting an iridium compound with an alkaline compound in a protic solvent to obtain a precipitate according to any one of items 1 to 7,
   (b) reacting the iridium containing precipitate in the presence of
      (i) at least one component selected from oxalic acid, a salt of oxalic acid, formic acid and a salt of formic acid, and
      (ii) at least one compound selected from $CH_3CO_2H$ and $CH_3(CO)O(CO)CH_3$
   to give an iridium acetate containing solution.
9. The process according to item 8, further comprising:
   (c) isolating the iridium acetate as a solid from the solution.
10. The process according to any one of items 8 or 9, wherein step (b) is conducted with heating.
11. The process according to any one of items 1 to 10, wherein the oxalic acid salt and/or the formic acid salt in steps (a) and (b) are independently selected from ammonium, alkali metal and alkaline earth metal salts.
12. The process according to any one of items 1 to 11, wherein the protic solvent used in steps (a) and/or (b) is independently selected from water, a $C_1$-$C_6$ alkanol and mixtures thereof.
13. The process according to any one of items 8 to 12, wherein the iridium containing precipitate used in step (b) is a freshly precipitated precipitate.
14. Iridium acetate as a solid, obtainable according to any one of items 9 to 13.
15. A solution, containing iridium acetate, obtainable according to any one of items 8 to 13.
16. A solution comprising (A) iridium acetate, (B) at least one compound selected from oxalic acid, a salt of oxalic acid, formic acid and a salt of formic acid, (C) at least one compound selected from $CH_3CO_2H$ and $CH_3(CO)O(CO)CH_3$ and (D) optionally a protic solvent.
17. An iridium containing precipitate, obtainable according to the process according to any one of items 1 to 7.
18. Use of an iridium acetate according to item 14 or of a solution according to item 15 or 16 or of a precipitate according to item 17 as a catalyst or as a catalyst precursor in homogeneously or heterogeneously catalyzed reactions, selected from carbonylation reactions, hydroformylation reactions, coupling reactions, oxidation reactions, hydrogenation reactions, and hydrosilylation reactions.
19. Use of a solid according to item 14 or of a solution according to item 15 or 16 or of a precipitate according to item 17 in electroplating.
20. Use of a solid according to item 14 or of a solution according to item 15 or 16 or of a precipitate according to item 17 for the preparation of catalysts for the heterogeneous catalysis.
21. A process as defined in any of items 1 to 7 for the preparation of an iridium containing precipitate having a low halide content.
22. The process according to item 21, wherein the iridium compound is an iridium chlorine compound.
23. The process according to item 21 or 22, wherein step (a) further comprises separating the obtained precipitate from the reaction mixture.
24. The process according to item 21 or 22, wherein step (a) further comprises washing of the separated precipitate until the halide content is less than 1000 ppm, preferably until the halide content is less than 800 ppm (based on Ir).
25. A process as defined in any of items 1 to 13 and 21 to 24 for the preparation of iridium acetate having a low halide content.
26. An iridium acetate, characterized in having a halide content of less than 1000 ppm, preferably less than 800 ppm (based on Ir).
27. The iridium acetate according to item 26, characterized in having a content of ammonium ions, alkali ions (i.e. Li, Na, K, Rb, Cs) or alkaline earth ions (i.e. Mg, Ca, Ba, Sr), respectively, below 1000 ppm, preferably below 500 ppm and particularly preferably below 300 ppm (based on Ir).
28. The iridium acetate according to item 26 or 27, characterized in having an absorption maximum ($\lambda_{max}$) at wavelengths shorter than 680 nm, preferably shorter than 675 nm and more preferably shorter than 670 nm in the visible/ultraviolet spectrum.
29. The iridium acetate according to any one of items 26 to 28, wherein the iridium acetate is a solid.
30. A solution comprising iridium acetate according to any one of items 26 to 29 and a suitable solvent.
31. The solution according to item 30, wherein the solvent is a protic solvent.
32. The solution according to item 30 or 31, further comprising:
   (i) at least one compound selected from the group consisting of oxalic acid, a salt of oxalic acid, formic acid and a salt of formic acid, and
   (ii) at least one compound selected from $CH_3COOH$ and $CH_3(CO)O(CO)CH_3$.
33. An iridium containing precipitate, characterized in having a halide content of less than 1000 ppm, preferably less than 800 ppm (based on Ir).
34. Use of iridium acetate according to any one of items 26 to 29 or of a solution according to any one of items 30 to 32 or of a precipitate according to item 33 as a catalyst or as a catalyst precursor in homogeneously or heterogeneously catalyzed reactions, selected from carbonylation reactions, hydroformylation reactions, coupling reactions, oxidation reactions, hydrogenation reactions, and hydrosilylation reactions.

35. Use of iridium acetate according to any one of items 26 to 29 or of a solution according to any one of items 30 to 32 or of a precipitate according to item 33 in galvanotechnics or for the preparation of catalysts for the heterogeneous catalysis.

EXAMPLES

The following examples serve to further explain the invention and are not to be construed as limiting. In the present invention "water" is understood as being water in its deionised form ("DI water").

Measuring Methods/Analytics

Visible/Ultraviolet Spectra

Measurement of the visible/ultraviolet spectra was conducted at room temperature using a UV spectrometer "Jena Specord 200" (tungsten lamp (VIS), deuterium lamp (UV)) and 1 cm cuvets (quartz glass cuvets "Soprasil", manufactured by Helma) in a measuring range of 200 nm to 1100 nm. Solid iridium acetate was dissolved in DI water in the concentrations indicated in FIGS. 1 and 2.

Determination of the Halide Content:

The determination of the halide (preferably chloride) content was conducted according to a method comprising the steps: (1) taking up the sample in a suitable solvent, (2) combustion in a oxyhydrogen flame, (3) collecting the condensate in a solution of sodium hydroxide and (4) determination of the halide content by ion chromatography (IC). This method is known by the designation "analysis of total halide content according to WICKBOLD".

Determination of the Content of Alkali Ions and Iridium:

The determination of the iridium content and of the content of any optionally contained alkali ions was conducted by ICP analysis in a manner known to one of ordinary skill in the art.

Example 1

Preparation of an Iridium Containing Precipitate (Step (a))

Apparatus: 1-L Standard Stirring Apparatus (Condenser, Mechanical Stirrer, Inert)

With stirring 50 g of iridium as ca. 4% by weight solution of $H_2IrCl_6$ were heated to about 95° C. with 4.0 g of oxalic acid and maintained at that temperature for about 2 hours. After addition of KOH (10% by weight in water, about 10 eq. based on Ir) within 20 minutes the reaction mixture was allowed to cool to room temperature. The pH was readjusted with acetic acid (50% by weight in water) to a value of approximately 7.5. Filtration through Blauband at room temperature and subsequent washing of the suspension with acetic acid (10% by weight in water) and DI water until the washing water was free of chlorine gave the product as a compact black solid.

An analysis of the filtrate by ion chromatography gave an iridium content of <1%, i.e., the yield based on iridium contained in the filter cake was >99%.

Example 2

Preparation of Iridium Acetate (Step (B))

Apparatus: 500-mL Standard Stirring Apparatus (Condenser, Mechanical Stirrer, Inert)

The filter cake obtained in step (a) together with 200 g of glacial acetic acid was placed in the apparatus and 2 g of formic acid were added. With stirring the reaction mixture was heated to reflux. At this temperature the reaction mixture was allowed to dissolve for 10 hours. After cooling to room temperature and filtration through Blauband the product was obtained as dark blue green solution. Removal of the solvent under vacuum yielded solid Ir-acetate as dark green crystals (yield: ca. 78-80%, based on iridium).

An analysis of the solution obtained in step (b) gave the following results: Cl<50 ppm, K<50 ppm, Ir ca. 2.5-3% by weight.

The visible/ultraviolet spectrum of the product shows an absorption maximum at $\lambda_{max}$=668.4 nm (cf. FIG. 2). The concentration of iridium acetate in DI water is 51.9 mg/50 ml (=1,038 mg/ml).

Example 3

Example 1 was repeated with the sole difference that in step (a) 50 g of iridium as ca. 4% by weight solution of $H_2IrCl_6$ were heated to about 95° C. with 4.0 g of oxalic acid and maintained at that temperature for about 90 minutes.

Step (b) was performed as described with respect to Example 2, whereby solid iridium acetate is obtained as dark green crystals (yield: 78-80%, based on iridium). The iridium acetate obtained is dissolved in DI water. The concentration of the solution obtained was 3.53% by weight of Ir.

Analytical Results a) total chlorine content according to WICKBOLD:
   Cl content (based on the solution): Cl=28 ppm
   Cl content (based on the Ir content): Cl=793 ppm
b) potassium content using ICP:
   K content (based on the solution) K<10 ppm (detection limit)
   K content (based on the Ir content) K<283 ppm (detection limit)

The visible/ultraviolet spectrum of the product shows an absorption maximum at $\lambda_{max}$=668.4 nm.

Example 4

Preparation of an Iridium Containing Precipitate (Step (a))

Apparatus: 1-L Standard Stirring Apparatus (Condenser, Mechanical Stirrer, Inert)

With stirring 50 g of iridium as ca. 4% by weight solution of $H_2IrCl_6$ were heated to about 98° C. with 4.0 g of oxalic acid and maintained at that temperature for about 90 minutes. After addition of KOH (10% by weight in water, about 10 eq. based on Ir) within 20 minutes the reaction mixture was allowed to cool to room temperature. The pH was readjusted with acetic acid (50% by weight in water) to a value of approximately 7.5. Filtration through Blauband at room temperature and subsequent washing of the suspension with acetic acid (10% by weight in water) and DI water until the washing water was free of chlorine gave the product as a compact black solid.

An analysis of the filtrate by ion chromatography gave an iridium content of <1%, i.e., the yield based on iridium contained in the filter cake was >99%.

Preparation of Iridium Acetate (Step (B))

Apparatus: 500-mL Standard Stirring Apparatus (Condenser, Mechanical Stirrer, Inert)

The filter cake obtained in step (a) together with 200 g of glacial acetic acid was placed in the apparatus and 2 g of formic acid were added. With stirring the reaction mixture was heated to reflux. At this temperature the reaction mixture was allowed to dissolve for 12 hours. After cooling to room temperature and filtration through Blauband the product was obtained as dark blue green solution. Removal of the solvent under vacuum yielded solid Ir-acetate as dark green crystals (yield: ca. 78%, based on iridium). The iridium acetate obtained is dissolved in DI water. The concentration of the solution was 4.06% by weight of Ir.

Analytical Results a) total chlorine content according to WICKBOLD:
  Cl content (based on the solution): Cl=30 ppm
  Cl content (based on the Ir content): Cl=739 ppm
The visible/ultraviolet spectrum of the product shows an absorption maximum at $\lambda_{max}$=668.2 nm. The concentration of iridium acetate in DI water is 0.744 mg/ml.

Comparative example

According to EP 1 046 629, Example 2

Apparatus: 100-mL Standard Stirring Apparatus (Condenser, Stirrer), Inert Gas Atmosphere 8.7 g of a ca. 23% by weight solution of $H_2IrCl_6$ were concentrated under vacuum at 55° C., until a viscous oil was formed. A black solid resulted after cooling to room temperature. This was taken up in 60 ml water and heated to 80° C. A dark solution formed, which was dropwise adjusted to pH 7.3 with 1n KOH solution. Here a black precipitate formed which was filtered still hot through Blauband. The filter cake was then washed with water using 100 ml portions until chlorine free. The filter cake was sucked dry. The resulting solid was suspended with 60 ml glacial acetic acid and heated to reflux for 23 hours. 2 hours prior to the end of the refluxing time further 15 ml of glacial acetic acid were added. After cooling to room temperature the resulting dark green solution was fine filtered through a G4 glass frit. After concentration of the solution under vacuum 2.5 g of a green solid (yield: 65%, based on iridium) formed.

An analysis of the product by ion chromatography gave an iridium content of 56.6% by weight (based on the solid).

Analytical Results

Total chlorine content according to WICKBOLD:
  Cl content (based on the solid): Cl=6% by weight (60000 ppm)
  Cl content (based on Ir) Cl=10.6% by weight (106000 ppm)
These values are markedly higher than the Cl contents of the iridium acetate of the present invention.

The visible/ultraviolet spectrum of the product shows an absorption maximum at $\lambda_{max}$=682 nm (cf. FIG. 1). The concentration of iridium acetate in DI water is 0.61 mg/ml.

Then invention claimed is:

1. An iridium acetate, characterized in having a halide content of less than 1000 ppm (based on Ir).

2. The iridium acetate according to claim 1, characterized in having contents of ammonium ions, alkali ions (i.e. Li, Na, K, Rb, Cs) or alkaline earth ions (i.e. Mg, Ca, Ba, Sr), respectively, of each below 1000 ppm (based on Ir).

3. The iridium acetate according to claim 1, characterized in having an absorption maximum ($\lambda_{max}$) at wavelengths shorter than 680 nm in the visible/ultraviolet spectrum.

4. The iridium acetate according to claim 1, wherein the iridium acetate is a solid.

5. A solution comprising iridium acetate according to claim 1 and a suitable solvent.

6. The solution according to claim 5, wherein the solvent is a protic solvent.

7. The solution according to claim 5, further comprising:
  (i) at least one compound selected from the group consisting of oxalic acid, a salt of oxalic acid, formic acid and a salt of formic acid; and
  (ii) at least one compound selected from $CH_3COOH$ and $CH_3(CO)O(CO)CH_3$.

8. An iridium containing precipitate, characterized in having a halide content of less than 1000 ppm, (based on Ir).

9. A process for the preparation of an iridium containing precipitate, the process comprising:
  (a) reacting an iridium compound with an alkaline compound in a protic solvent to obtain an iridium containing precipitate, wherein the reaction is conducted in the presence of at least one compound selected from oxalic acid, a salt of oxalic acid, formic acid and a salt of formic acid.

10. The process according to claim 9, wherein the iridium compound is an iridium halogen compound.

11. The process according to claim 10, wherein the iridium compound is an iridium chloro compound.

12. The process according to claim 9, wherein step (a) comprises separating the obtained precipitate from the reaction mixture.

13. The process according to claim 12, further comprising washing of the separated precipitate.

14. The process according to claim 12, wherein step (a) further comprises washing of the separated precipitate until the halide content is less than 1000 ppm (based on Ir).

15. The process according to claim 13, wherein washing is conducted until the washing liquid is free of halide ions.

16. The process according to claim 9, wherein the reaction in step (a) is conducted with heating.

17. The process according to claim 9, wherein the alkaline compound is selected from ammonium, alkali and alkaline earth hydroxides, carbonates and hydrogen carbonates and amines of the formula $NR^1R^2R^3$, wherein $R^1$, $R^2$ and $R^3$ are independently selected from a hydrogen atom and $C_1$-$C_6$ alkyl groups, and mixtures thereof.

18. A process for the preparation of iridium acetate comprising the steps of:
  (a) reacting an iridium compound with an alkaline compound in a protic solvent to obtain a precipitate according to claim 9,
  (b) reacting the iridium containing precipitate in the presence of
    (i) at least one component selected from oxalic acid, a salt of oxalic acid, formic acid and a salt of formic acid, and
    (ii) at least one compound selected from $CH_3CO_2H$ and $CH_3(CO)O(CO)CH_3$ to give an iridium acetate containing solution.

19. The process according to claim 18, further comprising:
  (c) isolating the iridium acetate as a solid from the solution.

20. The process according to claim 18, wherein step (b) is conducted with heating.

21. The process according to claim 18, wherein the oxalic acid salt and/or the formic acid salt in steps (a) and (b) are independently selected from ammonium, alkali metal and alkaline earth metal salts.

22. The process according to claim 18, wherein the protic solvent used in steps (a) and/or (b) is independently selected from water, a $C_1$-$C_6$ alkanol and mixtures thereof.

23. The process according to claim 18, wherein the iridium containing precipitate used in step (b) is a freshly precipitated precipitate.

24. A process for homogeneously or heterogeneously catalyzed reactions, selected from carbonylation reactions, hydroformylation reactions, coupling reactions, oxidation reactions, hydrogenation reactions, and hydrosilylation reactions, wherein iridium acetate having a halide content of less than 1000 ppm (based on Ir), or a solution thereof or a precipitate thereof is present as a catalyst or catalyst precursor.

25. In a process of electroplating or for the preparation of catalysts for heterogeneous catalysis, wherein iridium acetate having a halide content of less than 1000 ppm (based on Ir) or a solution thereof or a precipitate thereof is present.

26. The iridium acetate according to claim 1, wherein the halide content is less than 800 ppm (based on Ir).

27. The iridium acetate according to claim 1, characterized in having contents of ammonium ions, alkali ions (i.e. Li, Na, K, Rb, Cs) or alkaline earth ions (i.e. Mg, Ca, Ba, Sr), respectively, of each below 500 ppm (based on Ir).

28. The iridium acetate according to claim 1, characterized in having contents of ammonium ions, alkali ions (i.e. Li, Na, K, Rb, Cs) or alkaline earth ions (i.e. Mg, Ca, Ba, Sr), respectively, of each below 300 ppm (based on Ir).

29. The iridium acetate according to claim 8, wherein the halide content is less than 800 ppm (based on Ir).

30. The iridium acetate according to claim 12, wherein step (a) further comprises washing in of the separated precipitate until the halide content is less than 800 ppm (based on Ir).

* * * * *